US012668783B2

(12) United States Patent
Zhao et al.

(10) Patent No.: US 12,668,783 B2
(45) Date of Patent: Jun. 30, 2026

(54) PREPARATION METHOD AND APPLICATION OF VESICLE FORMED BY ERYTHROCYTE MEMBRANE ENCAPSULATING NEWCASTLE DISEASE VIRUS

(71) Applicant: Yongxiang Zhao, Nanning City (CN)

(72) Inventors: Yongxiang Zhao, Nanning City (CN); Liping Zhong, Nanning City (CN)

(73) Assignee: Yongxiang Zhao, Nanning City (CN)

( * ) Notice: Subject to any disclaimer, the term of this patent is extended or adjusted under 35 U.S.C. 154(b) by 763 days.

(21) Appl. No.: 18/043,315

(22) PCT Filed: Jun. 28, 2020

(86) PCT No.: PCT/CN2020/098632
§ 371 (c)(1),
(2) Date: Feb. 27, 2023

(87) PCT Pub. No.: WO2022/000145
PCT Pub. Date: Jan. 6, 2022

(65) Prior Publication Data
US 2025/0340849 A1        Nov. 6, 2025

(51) Int. Cl.
*C12N 7/00*        (2006.01)
*C12N 5/078*        (2010.01)

(52) U.S. Cl.
CPC ............. *C12N 7/00* (2013.01); *C12N 5/0641* (2013.01); *C12N 2509/10* (2013.01); *C12N 2760/18111* (2013.01)

(58) Field of Classification Search
None
See application file for complete search history.

(56) References Cited

FOREIGN PATENT DOCUMENTS

CN        108743615 A        11/2018
CN        109966266 A        7/2019

OTHER PUBLICATIONS

Muzykantov. V. R. "Drug delivery by red blood cells: vascular carriers designed by Mother Nature" Expert Opin Drug Deliv., vol. 7, No. 4, Apr. 30, 2020 (Apr. 30, 2020), pp. 404-405.
Shirrmacher, V. "Fifty Years of Clinical Application of Newcastle Disease Virus: Time to Celebrate!" Biomedicines, vol. 4, Jul. 20, 2016(Jul. 20, 2016), abstract, table 1.
谢晓田 等 (Xie, Xiaotian et al.),""红细胞膜包裹载药 PLGA 纳米颗粒的制 备及用于抑制 癌细胞的研究 (Preparation of RBCM-encapsulated drug-loaded PLGA nanoparticles and its application in inhibiting cancer cells)" 化工新型材料 (New Chemical Materials), vol. 47, No. 12, Dec. 31, 2019(Dec. 31, 2019), p. 216 left-hand column paragraph 1.
Ran, L. et al. "Delivery of oncolytic adenovirus into the nucleus of tumorigenic cells by tumor microparticles for virotherapy" Biomaterials, vol. 89, Feb. 23, 2016 (Feb. 23, 2016) pp. 56-66.
黄际薇 等 (Huang, Jiwei et al.) ""一个新型的药物 递送系统—红细 胞膜仿生纳米粒 (A Novel Drug Delivery System—Red Blood Cell Membranes Biomimetic Nanoparticles)" 中山大学学报 （（自然科学版）） (Acta Scientiarum Naturalium Universitatis Sunyatseni), vol. 58, No. 5, Sep. 30, 2019(Sep. 30, 2019), pp. 114-118.

*Primary Examiner* — Nicole Kinsey White
*Assistant Examiner* — Ruixue Wang

(57)        ABSTRACT

The present disclosure proposes a preparation method of a vesicle formed by an erythrocyte membrane encapsulating Newcastle disease virus, including: mixing a compacted erythrocyte solution, a phosphate buffered saline (PBS) solution, and Newcastle disease virus (NDV); centrifuging a resulting mixture of erythrocytes added with NDV; and resuspending and precipitating the centrifuged mixture with a PBS solution to obtain the vesicle formed by the erythrocyte membrane encapsulating Newcastle disease virus.

4 Claims, 3 Drawing Sheets

PREPARATION METHOD AND APPLICATION OF VESICLE FORMED BY ERYTHROCYTE MEMBRANE ENCAPSULATING NEWCASTLE DISEASE VIRUS

TECHNICAL FIELD

The present disclosure relates to the field of medical medicine technologies, in particular to a preparation method and an application of a vesicle formed by an erythrocyte membrane encapsulating Newcastle disease virus.

BACKGROUND

Lysovirus is a virus that replicates specifically in tumor cells only, kills tumor cells, and has no damaging effect on human normal, which is an emerging tumor treatment. Although lysovirus therapy is safe, there are some problems that need to be solved. First, how to avoid neutralization by antibodies produced by the body during the treatment process. The lysozyme virus has strong immunogenicity, which makes the body produce antibodies, and the virus entering the body is easily neutralized by antibodies when administered again, which reduces the viral potency and leads to the failure of tumor treatment. Second, the antiviral defense mechanism in tumor cells will resist the entry of lysozyme virus into the cells and reduce the efficiency of killing.

Microparticles (MPs) are vesicle-like particles with a particle size of 100-1000 nm, which are released outside the cell by the cell membrane wrapping the cell contents in a "sprouting" manner due to cytoskeleton changes during the process of cell activation or apoptosis. As a natural carrier, vesicles can encapsulate chemotherapeutic drugs, lysovirus, etc.

SUMMARY OF THE DISCLOSURE

Technical Problem

The technical problem to be solved by the present disclosure is to provide a preparation method and an application of a vesicle formed by an erythrocyte membrane encapsulating Newcastle disease virus for the defect that lysovirus of the related art is easily neutralized and killed by antibodies produced by the body during the treatment process with low efficiency.

Technical Solution

To solve the above technical problem, the technical solution proposed by the present disclosure is to provide a preparation method of a vesicle formed by an erythrocyte membrane encapsulating Newcastle disease virus, including:

mixing a compacted erythrocyte solution, a phosphate buffered saline (PBS) solution, and Newcastle disease virus (NDV);

centrifuging a resulting mixture of erythrocytes added with NDV; and resuspending and precipitating the centrifuged mixture with a PBS solution to obtain the vesicle formed by the erythrocyte membrane encapsulating Newcastle disease virus.

In some embodiments, the compacted erythrocyte solution is obtained by:

diluting anticoagulated whole blood with an equal volume of PBS solution, separating erythrocyte, and removing a supernatant by centrifugation; and adding a PBS solution to wash, and removing a supernatant by centrifugation to obtain the compacted erythrocyte solution.

In some embodiments, the mixing a compacted erythrocyte solution, a phosphate buffered saline (PBS) solution, and Newcastle disease virus (NDV) includes:

adding 10 mL of PBS solution and 4 mL NDV to each mL of the compacted erythrocyte solution, mix well, and observe for hemagglutination after 1 hour, with hemagglutination and no erythrocyte deposition.

In some embodiments, the centrifuging a resulting mixture of erythrocytes added with NDV includes:

collecting the mixture of erythrocytes with NDV and add the mixture into a 50 mL centrifuge tube;

centrifuging at 1300 rpm 4° C. for 8 min, centrifuging at 5000 rpm 4° C. for 15 min;

transferring a supernatant to another centrifuge tube and centrifuging at 14000 g 4° C. for 2 min; and transferring a supernatant to another centrifuge tube and centrifuging at 14000 g 4° C. for 1 h.

In some embodiments, the resuspending and precipitating the centrifuged mixture with a PBS solution to obtain the vesicle formed by the erythrocyte membrane encapsulating Newcastle disease virus includes:

discarding a supernatant, resuspending and precipitating in 1 mL of PBS, and centrifuging at 14000 g 4° C. for 30 min; and discarding a supernatant, resuspending and precipitating in 1 mL of PBS, and storing at −20° C.

The present disclosure further provides a vesicle formed by an erythrocyte membrane encapsulating Newcastle disease virus prepared by the method as above.

The present disclosure further provides an application of the vesicle formed by erythrocyte membrane encapsulating Newcastle disease virus as above in tumor therapy.

BENEFICIAL EFFECT

The preparation method and application of a vesicle formed by an erythrocyte membrane encapsulating Newcastle disease virus proposed by the present disclosure have the following technical effect: the vesicle takes advantage of the presence of abundant sialic acid receptors on the surface of the erythrocyte membrane, and after binding to the HN protein of NDV, it can firstly close the neutralizing antibody site; secondly, NDV can enter the interior of the erythrocyte, which further avoids NDV stimulating the host's antiviral immune response; thirdly, the "don't eat me" protein CD47 on the erythrocyte membrane can directly interact with the signal regulatory protein α (SIRPα) on the surface of phagocytes to send "don't eat me" signals, thereby inhibiting the phagocytic clearance function of macrophages and improving the efficacy of the drug.

BRIEF DESCRIPTION OF THE DRAWINGS

In order to more clearly illustrate the technical solutions in the specific embodiments of the present disclosure or the related art, the following will briefly introduce the accompanying drawings that need to be used in the specific embodiments or related art. It is obvious that the attached drawings in the following description are some of the embodiments of the present disclosure. For those skilled in the art, other accompanying drawings may be obtained from these drawings without creative effort.

DETAILED DESCRIPTION

Figure 1:
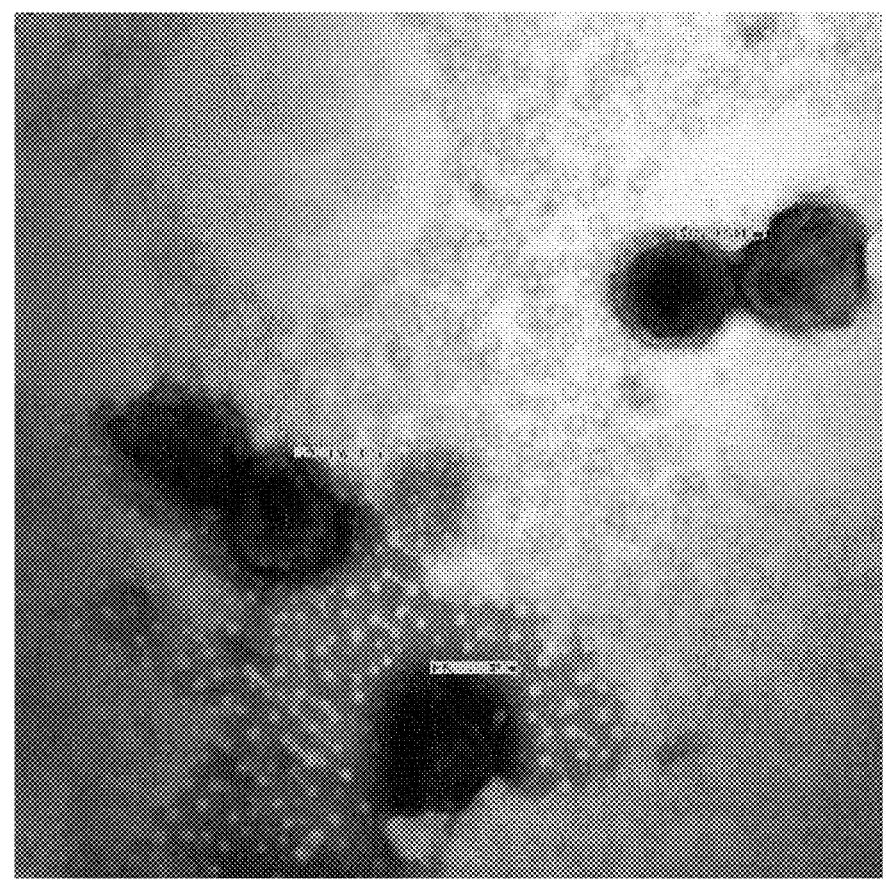
FIG. 1 is a scanning electron micrograph of NDV-MPs according to an embodiment of the present disclosure, with the diameter of NDV-MPs around 200 nm between scanning electron microscopes, are shown in FIG. 1.

In order to facilitate the understanding of the present disclosure, the present disclosure will be more fully described below with reference to the relevant accompanying drawings. Exemplary embodiments of the present disclosure are given in the accompanying drawings. However, the present disclosure can be implemented in many different forms and is not limited to the embodiments described herein. Rather, these embodiments are provided for the purpose of making the present disclosure more thorough and comprehensive.

Unless otherwise defined, all technical and scientific terms used herein have the same meaning as commonly understood by those skilled in the art belonging to the present disclosure. The terms used herein in the specification of the present disclosure are used only for the purpose of describing specific embodiments and are not intended to limit the present disclosure.

The present disclosure provides a preparation method of a vesicle formed by an erythrocyte membrane encapsulating Newcastle disease virus. The method includes the following operations.

Mixing a compacted erythrocyte solution, a phosphate buffered saline (PBS) solution, and Newcastle disease virus (NDV).

Specifically, in some embodiments, discarding a supernatant, resuspending and precipitating by 1 mL of PBS solution, followed by centrifugation at 14,000 g for 30 min at 4° C.

Centrifuging a resulting mixture of erythrocytes added with NDV.

Specifically, in some embodiments, collecting the mixture of erythrocytes added with NDV into a 50 mL centrifuge tube; centrifuging the mixture at 1300 rpm 4° C. for 8 min and at 5000 rpm 4° C. for 15 min; transferring a supernatant to another centrifuge tube and centrifuging at 14000 g 4° C. for 2 min; transferring a supernatant to another centrifuge tube and centrifuging at 14000 g for 1 h at 4° C.

Resuspending and precipitating the erythrocyte mixture after centrifugation with the PBS solution to obtain the vesicle formed by the erythrocyte membrane encapsulating Newcastle disease virus.

Specifically, in some embodiments, discarding a supernatant, resuspending and precipitating by 1 mL of PBS solution, followed by centrifugation at 14,000 g for 30 min at 4° C.; discarding a supernatant, resuspending and precipitating by 1 mL of PBS solution, and storing at −20° C.

The present disclosure has no special requirements on the source of erythrocyte, and any method of obtaining erythrocyte known to those skilled in the art is possible. The erythrocyte described in the present disclosure is prepared and obtained according to the following methods: anticoagulated whole blood is diluted with an equal volume of PBS solution, then the erythrocyte is separated, and a supernatant is removed by centrifugation; the PBS solution is added and washed, and a supernatant is removed by centrifugation to obtain the compacted erythrocyte solution. There is no special requirement for the method of centrifugation in the present disclosure, and the person skilled in the art can choose a suitable centrifugation method and time according to the actual situation.

The present disclosure also provides a vesicle formed by an erythrocyte membrane encapsulating Newcastle disease virus made by the above preparation method. The vesicle takes advantage of the presence of abundant sialic acid receptors on the surface of the erythrocyte membrane, and after binding to the HN protein of NDV, it can firstly close the neutralizing antibody site; secondly, NDV can enter the interior of the erythrocyte, which further avoids NDV stimulating the host's antiviral immune response; thirdly, the "don't eat me" protein CD47 on the erythrocyte membrane can directly interact with the signal regulatory protein α (SIRPα) on the surface of phagocytes to send "don't eat me" signals, thereby inhibiting the phagocytic clearance function of macrophages and improving the efficacy of the drug. Therefore, the vesicle formed by erythrocyte membrane encapsulating Newcastle disease virus prepared by the present disclosure can be used for tumor therapy.

In order to better understand the above technical solutions, the above technical solutions will be described in detail in the following with the accompanying drawings of the specification and specific embodiments, and it should be understood that the embodiments of the present disclosure and the specific features in the embodiments are detailed descriptions of the technical solutions of the present disclosure, not limitations of the technical solutions of the present disclosure. The embodiments of the present disclosure and the technical features in the embodiments can be combined with each other without conflict.

Embodiment 1 Preparation of a Vesicle Formed by Erythrocyte Membrane Encapsulating Newcastle Disease Virus 1. Anticoagulated whole blood diluted with an equal volume of PBS.
2. Separate erythrocytes: centrifuge at 2500 r/min for 10 min, remove supernatant.
3. Add an equal volume of PBS to the compacted erythrocytes and wash, centrifuge at 2500 r/min for 10 min, remove supernatant.
4. Erythrocyte counting, dilute erythrocytes to $6*10^9$/mL.
5. Prepare 1 mL of compacted erythrocytes+99 mL PBS into 1% erythrocyte suspension, conduct hemagglutination experiment, calculate the hemagglutination potency of NDV as $2^7$.
6. Add 10 mL PBS and 4 mL NDV to each mL of compacted erythrocytes, mix, and observe for hemagglutination after 1 hour, with hemagglutination and no erythrocyte deposition.
7. Collect the erythrocyte mixture with NDV and add into a 50 mL centrifuge tube.
8. Centrifuge at 1300 rpm 4° C. for 8 min, centrifuge at 5000 rpm 4° C. for 15 min.
9. Transfer the supernatant to another centrifuge tube and centrifuge at 14000 g 4° C. for 2 min.
10. Transfer the supernatant to another centrifuge tube and centrifuge at 14000 g 4° C. for 1 h.

11. Discard the supernatant, resuspend and precipitate in 1 mL of PBS, and centrifuge at 14000 g 4° C. for 30 min.

12. Discard supernatant, resuspend and precipitate in 1 mL of PBS, store at –20° C.

Embodiment 2 RBC MPs PKH26 Staining Test

Figure 2:
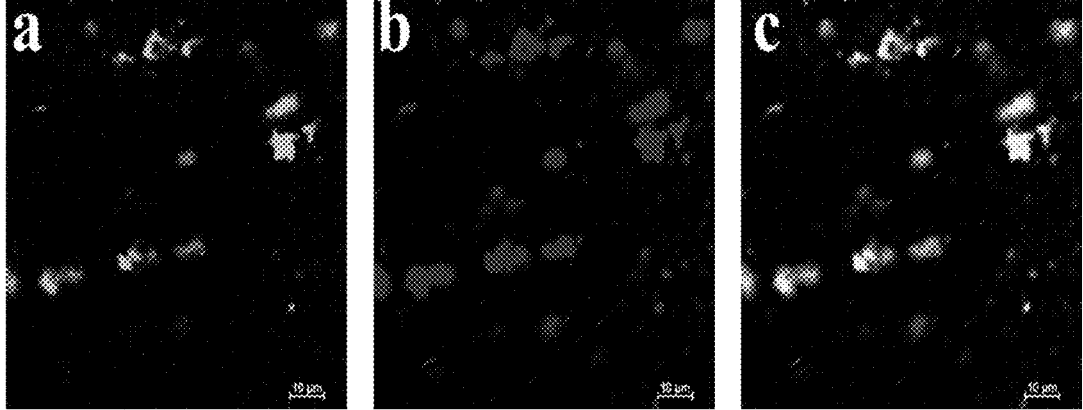
FIG. 2 is laser confocal images of RBC MPs CD63 after staining, where a: RBC MPs incubated with CD63 antibody; b: NDV-Cherry with red fluorescence; c: green and red superimposed into orange.

1. Centrifuge the prepared 200 mL RBC MPs with RBC encapsulating NDV-EGFP at 14000 g for 30 min at 4° C.
2. Resuspend RBC MPs using 200 mL diluent C.
3. Mix 200 mL diluent C with 3 mL PKH26 stain, mix well.
4. Add the mixture of 200 mL diluent C and PKH26 stain to RBC MPs.
5. Stain at room temperature for 1 h, shake every 15 min.
6. Add an equal volume of serum to neutralize the reaction.
7. Centrifuge at 14000 g for 30 min at 4° C.
8. Discard the supernatant, resuspend and precipitate in 1 mL of PBS, and centrifuge at 14000 g for 30 min at 4° C.
9. Discard the supernatant, resuspend and precipitate in 200 mL of PBS, and conduct laser confocal detection; the results are shown in FIG. 2, where RBCs bind well with MPs.

Embodiment 3 In Vitro Killing Experiments

1. Wash HepG2 cells with 90% growth density once with PBS, digest with 0.25% EDTA trypsin, centrifuge at 800 rpm for 3 min, discard the supernatant, wash once with PBS, resuspend HepG2 cells in DMEM containing 10% FBS, and count.
2. Add 100 μL of cell suspension into 96-well plate, $1*10^3$ cells per well, incubate at 37° C. in 5% $CO_2$ incubator.
3. After 12 hours, observe the cell growth density of about 30%, aspirate the original medium and add 90 μL of DMEM containing 2% FBS.
4. Add 10 uL of PBS, RBC MPs, NDV, respectively, and incubate at 37° C., 5% $CO_2$ incubator.
5. Add CCK8 10 uL at 24 h, 48 h, 72 h, 96 h, respectively, incubate at 37° C., 5% $CO_2$ incubator for 2 h, and detect the absorbance by enzyme marker to detect cell viability.

Figure 3:
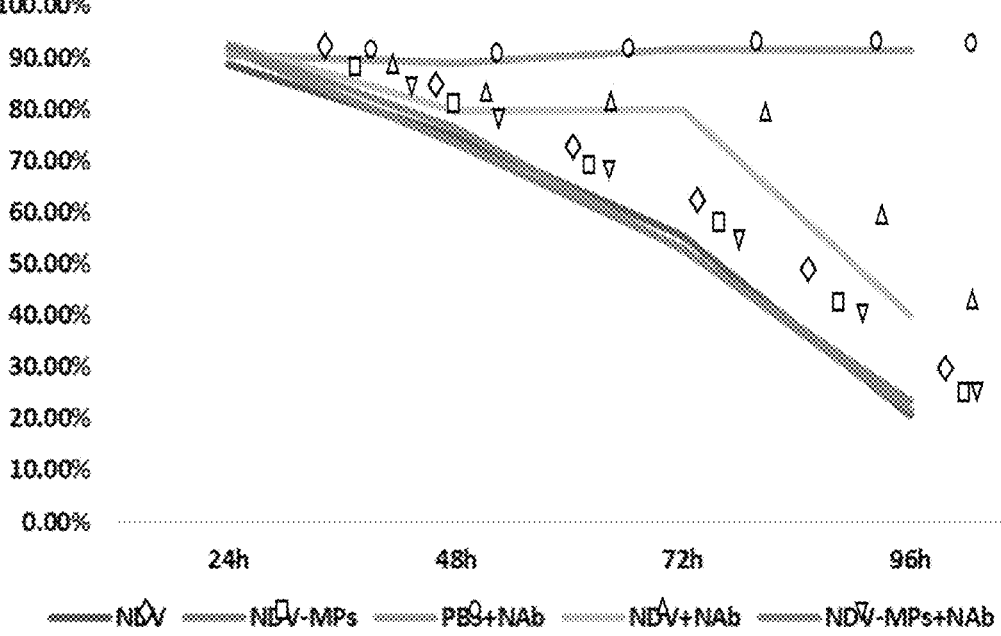
FIG. 3 illustrates results of in vitro cell killing experiments.

As shown in FIG. 3, the in vitro cell killing experiments confirm that NDV-MPs can circumvent the neutralization reaction of anti-NDV neutralizing antibody and have stronger killing effect.

The embodiments of the present disclosure have been described above in conjunction with the accompanying drawings, but the present disclosure is not limited to the above specific embodiments, which are merely schematic and not limiting, and many other forms can be made by those skilled in the art under the inspiration of the present disclosure without departing from the scope protected by the purpose and claims of the present disclosure, all of which fall within the scope of the present disclosure.

What is claimed is:

1. A preparation method of a vesicle formed by an erythrocyte membrane encapsulating Newcastle disease virus, comprising:

mixing a compacted erythrocyte solution, a phosphate buffered saline (PBS) solution, and Newcastle disease virus (NDV);

centrifuging the resulting mixture of erythrocytes added with NDV; and resuspending the centrifuged pellet of the resulting mixture in a PBS solution to obtain the vesicle formed by the erythrocyte membrane encapsulating Newcastle disease virus;

wherein the compacted erythrocyte solution is obtained by:

diluting anticoagulated whole blood with an equal volume of PBS solution, separating erythrocyte, and removing the supernatant by centrifugation; and adding a PBS solution to wash, and removing a supernatant by centrifugation to obtain the compacted erythrocyte solution;

wherein step of centrifuging the resulting mixture of erythrocytes added with NDV comprises:

collecting the mixture of erythrocytes with NDV and add the mixture into a 50 mL centrifuge tube;

centrifuging at 1300 mm 40° C. for 8 min, and then centrifuging at 5000 mm 40° C. for 15 min;

transferring the supernatant to another centrifuge tube and centrifuging at 14000 g 4° C. for 2 min; and transferring the supernatant to another centrifuge tube and centrifuging at 14000 g 4° C. for 1 h;

wherein the step of resuspending the centrifuged pellet of the resulting mixture in a PBS solution to obtain the vesicle formed by the erythrocyte membrane encapsulating Newcastle disease virus comprises:

discarding the supernatant, resuspending the centrifuged pellet of the resulting mixture in 1 mL of PBS, and centrifuging at 14000 g 4° C. for 30 min; and discarding the supernatant, resuspending the centrifuged pellet of the resulting mixture in 1 mL of PBS, and storing at –20° C.

2. The method according to claim 1, wherein the step of mixing a compacted erythrocyte solution, a phosphate buffered saline (PBS) solution, and Newcastle disease virus (NDV), comprises:

adding 10 mL of PBS solution and 4 mL NDV to each mL of the compacted erythrocyte solution, mix well, observing for hemagglutination after 1 hour, and retaining the mixture of erythrocytes with NDV when hemagglutination is observed and no erythrocyte deposition occurs, wherein the hemagglutination potency of NDV is $2^7$.

3. A vesicle formed by an erythrocyte membrane encapsulating Newcastle disease virus prepared by the method according to claim 1.

4. A vesicle formed by an erythrocyte membrane encapsulating Newcastle disease virus prepared by the method according to claim 2.

* * * * *